(12) United States Patent
Takashi et al.

(10) Patent No.: US 7,927,101 B2
(45) Date of Patent: Apr. 19, 2011

(54) HANDPIECE AND METHOD FOR PREVENTING OCCURENCE OF SUCKING-BACK IN THE HANDPIECE

(75) Inventors: Tetsuya Takashi, Kyoto (JP); Shozo Nakayama, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 11/886,975

(22) PCT Filed: Mar. 22, 2006

(86) PCT No.: PCT/JP2006/305716
§ 371 (c)(1),
(2), (4) Date: Dec. 17, 2007

(87) PCT Pub. No.: WO2006/101133
PCT Pub. Date: Sep. 28, 2006

(65) Prior Publication Data
US 2009/0029312 A1    Jan. 29, 2009

(30) Foreign Application Priority Data

Mar. 22, 2005   (JP) ................................ 2005-082098

(51) Int. Cl.
*A61C 1/05*   (2006.01)
(52) U.S. Cl. ........................................ 433/132; 415/904
(58) Field of Classification Search .................. 433/132; 415/904
See application file for complete search history.

(56) References Cited

U.S. PATENT DOCUMENTS

| 5,567,154 | A | 10/1996 | Wohlgemuth |
| 6,120,291 | A | 9/2000 | Bareth et al. |
| 6,676,374 | B2 * | 1/2004 | Hashimoto et al. ........... 415/202 |
| 2004/0018467 | A1 | 1/2004 | Tanaka et al. |

FOREIGN PATENT DOCUMENTS

| CN | 1456129 | 11/2003 |
| JP | 52-118893 | 10/1977 |
| JP | 6-20492 | 6/1994 |
| JP | 6-28086 | 8/1994 |
| JP | 8-569958 | 3/1996 |
| JP | 09-108239 | 4/1997 |
| JP | 09-122146 | 5/1997 |
| JP | 2000-60870 | 2/2000 |
| JP | 2000-060870 | 2/2000 |
| JP | 2000-126203 | 5/2000 |
| JP | 2003-325546 | 11/2003 |

* cited by examiner

*Primary Examiner* — Cris L Rodriguez
*Assistant Examiner* — Eric Rosen
(74) *Attorney, Agent, or Firm* — DLA Piper LLP (US)

(57) ABSTRACT

A handpiece and a method for driving the handpiece are provided in which a sucking-back problem can be prevented with a simple structure. The handpiece 10 has a gripping portion 11 to be gripped by an operator, a head 15 mounted at a distal end of the gripping portion; and a wheel 55 rotatably mounted in an interior of the head. The head has an inlet 25 from which air is supplied to the wheel and an outlet 28 from which the air is discharged, the inlet and outlet being defined in the head, at least one buffer chamber 47 defined in the head, where the air is forced in due to a centrifugal force applied thereto by rotations thereof with the wheel and then accumulated under positive pressure, passages 66, 67, 68, and 34 for guiding the accumulated air from a neighborhood of the rotating wheel to an atmosphere, and a circumferential wall 44 mounted between the outlet and the wheel for providing a resistance to the air moving from the wheel toward the outlet.

6 Claims, 9 Drawing Sheets

HANDPIECE AND METHOD FOR PREVENTING OCCURENCE OF SUCKING-BACK IN THE HANDPIECE

FIELD OF THE INVENTION

The present invention relates to a handpiece and a method for preventing occurrence of sucking back in the handpiece. In particular, the present invention relates to an air-driven medical and dental handpiece (hereinafter referred to as "medical handpiece") which rotates a cutting tool by means of pressurized air and a method for preventing occurrence of sucking-back in the medical handpiece.

BACKGROUND OF THE INVENTION

According to the conventional and widely used air-driven handpieces, pressurized air is impinged onto a wheel rotatably accommodated within a distal head of the handpiece to rotate the wheel and the cutting tool retained by the wheel. In those air-driven handpieces, the rotation of the wheel is maintained for a while by force of inertia even after the completion of the supply of the pressurized air. During the inertial rotation, although the air supply through the supply inlet is stopped, the air rotating with the wheel is forced out into the outlet, which in turn causes an interior of the head to be evacuated in part or in whole. This results in that contaminations adhering on or existing around the cutting tool such as saliva, blood, and/or cutting debris of the teeth may be sucked back through small gaps between the head and the tool into the interior of the head and then the air outlet, so that the contaminations would be accumulated within the interiors of the handpiece and air-supply tube, which has been known to the art as "sucback" or "sucking-back".

For preventing the occurrence of such sucking-back, there have been proposed a various techniques so far. For example, Document 1 (JUM 6-20492 B) and Document 2 (JP 9-122146 A) disclose a technique for preventing the contamination of the handpiece, in which a low pressure air is fed into the de-energized handpiece to maintain a positive pressure within the interior of the handpiece. This, however, does not relate to the structural solution to the sucking-back problems.

Document 3 (JP 9-108239 A) discloses another technique in which a movable valve is mounted in the handpiece, by which the air discharge is halted with the stop operation of the wheel. The movable valve can be inoperative by the repetition of the sterilizations of the handpiece, which may fail to effectively attain the prevention of the sucking-back.

Document 4 (JP 2000-60870 A) discloses a handpiece in which a projection is provided on the upstream side of the air outlet with respect to the rotational direction of the wheel in order to prevent the pressurized air from being discharged into the air outlet. With the arrangement, the air outlet is opposed to the wheel, which unavoidably causes a negative pressure in the air outlet by the inertial rotation of the wheel and then is incapable of preventing the generation of the sucking-back effectively.

Document 5 (JP 6-28086 B) discloses a handpiece in which the contaminations such as cutting debris within the handpiece are discharged with an aid of centrifugal force through the contamination discharge pass into the atmosphere. Also, Document 6 (JP 2000-126203) discloses a handpiece in which a member is provided on the bearing for preventing the contaminations such as cutting debris from entering into the interior of the handpiece. These handpieces, however, are incapable of effectively preventing the invasions of the saliva and blood including contaminated small particles and mist thereof into the interior of the handpiece.

SUMMARY OF THE INVENTION

A purpose of the present invention is to provide a handpiece and its driving method by which the sucking-back is completely avoided for a long period of time, with a simple structure.

For this purpose, a handpiece according to the present invention has a gripping portion to be gripped by an operator;
 a head mounted at a distal end of the gripping portion; and
 a wheel rotatably mounted in an interior of the head;
 wherein the head having
  an inlet from which air is supplied to the wheel and an outlet from which the air is discharged, the inlet and outlet being defined in the head;
  at least one buffer chamber defined in the head, where the air is forced in due to a centrifugal force applied thereto by rotations thereof with the wheel and then accumulated under positive pressure;
  a passage for guiding the accumulated air from a neighborhood of the rotating wheel to an atmosphere; and
  a circumferential wall mounted between the outlet and the wheel for providing a resistance to the air moving from the wheel toward the outlet.

A first aspect of the present invention provides a handpiece in which the buffer chamber is opened to oppose a rotational direction of the wheel.

A second aspect of the present invention provides a handpiece in which the buffer chamber is oriented to a direction defining an angle of about 30-60 degrees with a tangential line defined on a circle drawn by a rotating outermost edge of the wheel.

A third aspect of the present invention provides a handpiece in which the circumferential wall substantially occupies a region where the outlet opposes the wheel.

A fourth aspect of the present invention provides a handpiece in which the buffer chamber is formed adjacent to and on an upstream side of the outlet with respect to the rotation of the wheel.

A fifth aspect of the present invention provides a handpiece in which the head has an external housing and an internal housing, the external housing having an interior within which the internal housing is releasably mounted, the internal housing having an interior within which the wheel is accommodated, the buffer chamber and the circumferential wall being formed on the internal housing.

A method for preventing sucking-back according to the present invention has
 rotatably mounting a wheel in a head mounted at a distal end of a gripping portion to be gripped by an operator;
 rotating the wheel and a tool held by the wheel using an air ejected from an inlet; and
 discharging the air rotating with the wheel through an outlet;
 wherein, during an inertial rotation of the wheel after a halt of an air ejection from the inlet to the wheel,
 restricting a flow of the air moving from the wheel to the outlet by a wall provided between the wheel and the outlet;
 causing the air rotating with the wheel to be compressively forced into a buffer chamber formed outside the wheel due to a centrifugal force applied thereto; and discharging the compressed air radially outwardly from the tool through a passage formed in the head to an atmosphere.

ADVANTAGES

According to the handpiece and the method for prevention of sucking back, even during the inertial rotations of the wheel after the halt of air supply, the buffer chamber is maintained as it is pressurized and therefore the pressurized air is discharged to the atmosphere. This means that, during the inertial rotations of the wheel after the halt of supply of the driving air, no contaminations adhering on the tool and/or existing around the tool will be drawn into interior of the handpiece, which always maintains the interiors of the handpiece and the supply tube clean With the first and second aspect of the handpiece according to the present invention, since the buffer chamber is opened to oppose a rotational direction of the wheel, the air is effectively forced into the buffer chamber to maintain the buffer at high pressure.

With the third aspect of the handpiece according to the present invention, since the circumferential wall substantially occupies a region where the outlet opposes the wheel, the air rotating with the wheel is not forced into the outlet during the inertial rotations thereof but forms an air flow from the outlet toward the wheel.

With the fourth aspect of the handpiece according to the present invention, since the buffer chamber is formed adjacent to and on the upstream side of the outlet with respect to the rotation of the wheel, the air from the wheel is effectively accelerated into the buffer chamber to maintain a sufficiently pressurized condition within the buffer chamber.

With the fifth aspect of the handpiece according to the present invention, the buffer chamber and the circumferential wall can be formed easily.

DETAILED DESCRIPTION OF THE PREFERRED EMBODIMENTS

Figure 1:
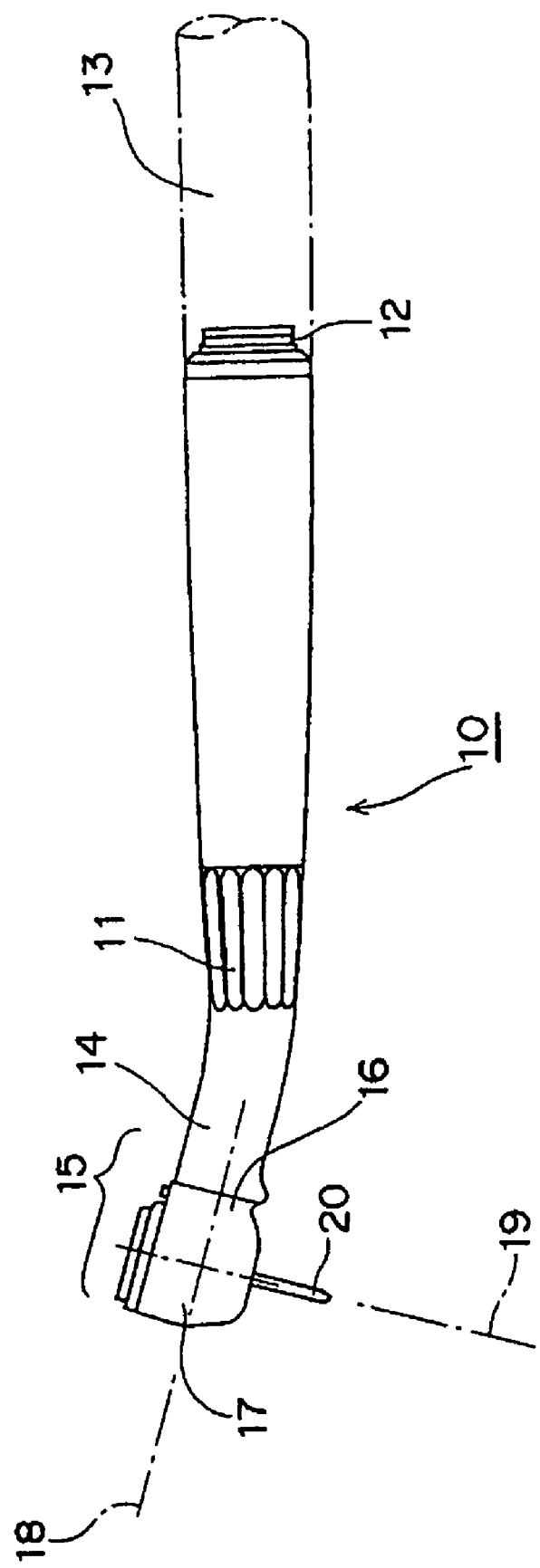
FIG. 1 is a side elevational view of a handpiece of the present invention.

Referring to the drawings, a handpiece and a sucking-back prevention method therefor will be described below. Note that the like reference numerals indicate like parts throughout several drawings used in the following descriptions.

[1] General Construction

FIG. 1 is a side elevational view showing an overall structure of the handpiece according to the present invention. In this drawing, a handpiece generally indicated at 10 has a gripping portion 11 to be gripped by a hand of the operator during medical operations. The gripping portion 11 has one end in the form of a connection 12 to which a supply tube 13 receiving a plurality of flexible tubes (not shown) for supplying materials such as air and water is connected and the other end in the form of a neck 14 to which a head 15 described below is attached.

The head 15 integrally includes a stem 16 and a cylindrical external housing 17 for accommodating a cutting tool rotating mechanism 21 (see FIG. 2) described below. In this embodiment, a central axis 19 of the external housing 17 is oriented perpendicular to or substantially perpendicular to a longitudinal axis 18 of the stem 16. The central axis 19 corresponds to a rotational axis of a cutting tool 20 and therefore will be referred to as "rotational axis" below.

[2] Stem of the Head

Figure 2:
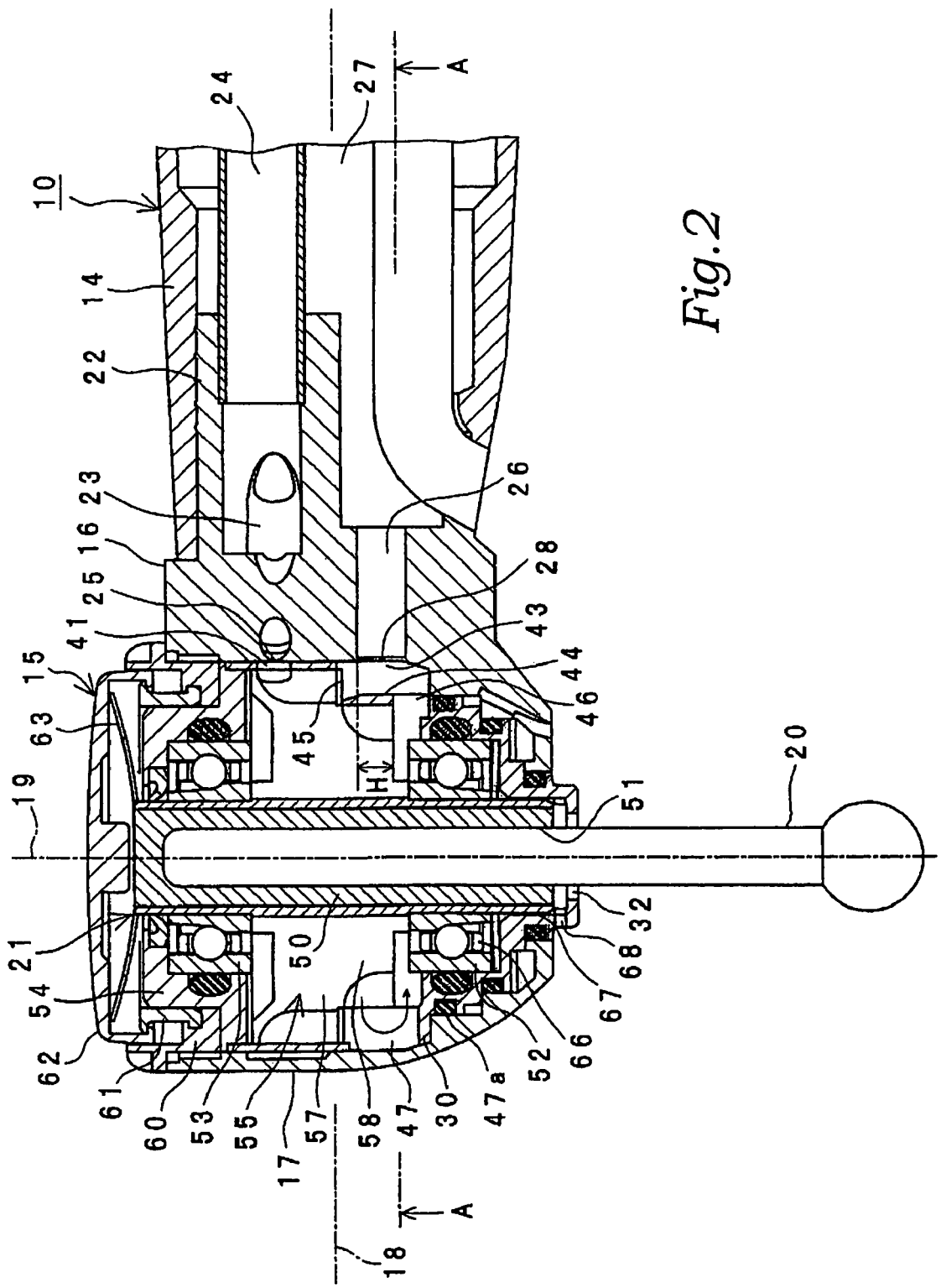
FIG. 2 is a partial enlarged cross sectional view of the handpiece in FIG. 1.
Figure 3:
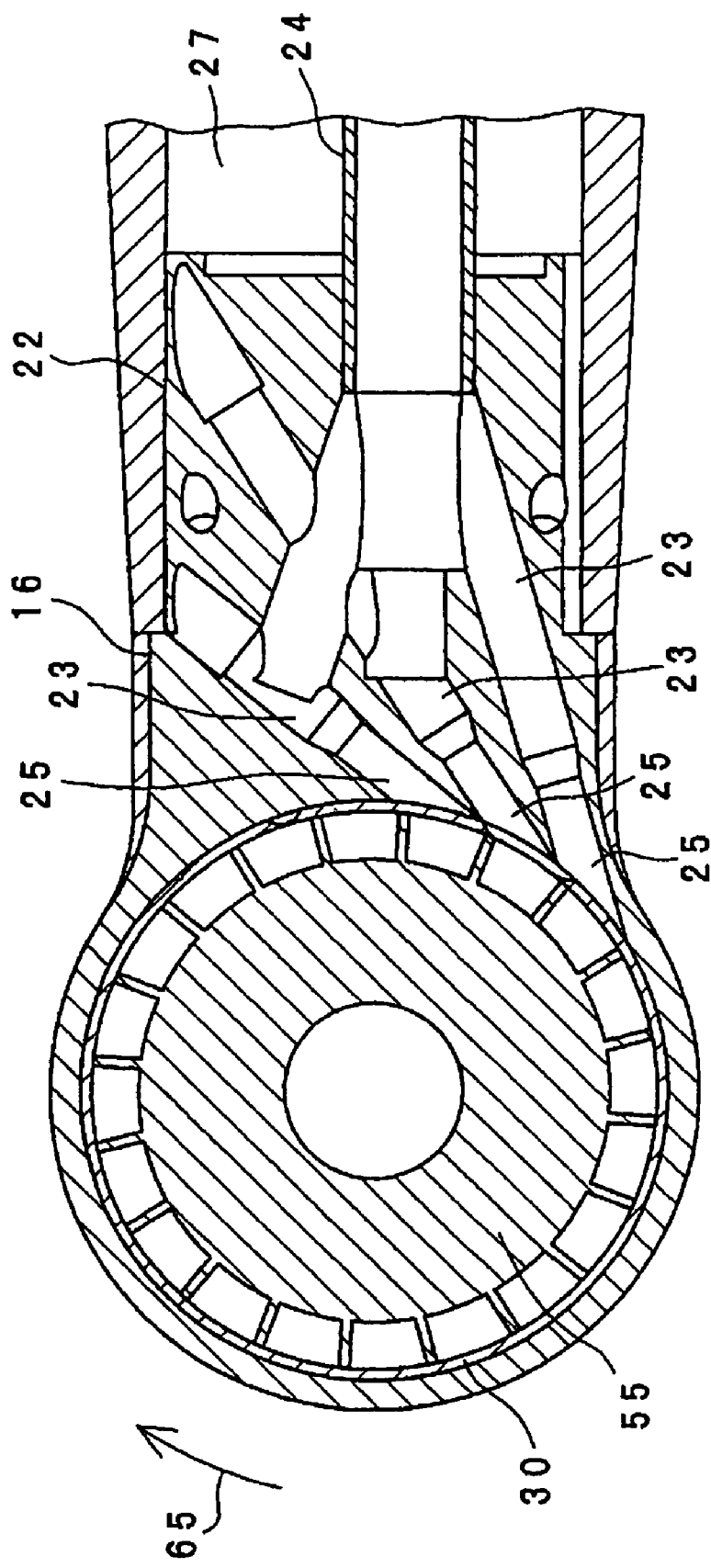
FIG. 3 is a partial enlarged cross sectional view of the handpiece in FIG. 1.

Referring to FIG. 2, the stem 16 of the head 15 has a portion 22 with a reduced cross section which is so sized and shaped to be inserted, in and secured to the distal end portion of the gripping portion 11. Referring next to FIG. 3, the stem 16 has a plurality of air passages (air supply nozzles) 23 defined therein for supplying driving air to the cutting tool mechanism 21. One ends of the air passages 23 (i.e., right ends in the drawing) are fluidly communicated to an air supply tube 24 which in turn is communicated to another air supply tube (not shown) accommodated within the supply tube 13. The other ends of the air supply passages 23 are oriented to the rotational direction of the cutting tool 20 (i.e., clockwise direction in FIG. 3) so that air ejected from the air inlets 25 of the air supply passages 23 can be used effectively for the rotation of the cutting tool 20. Referring back to FIG. 2, the stem 16 also has a discharge passage 26 defined therein for discharging air from the cutting tool mechanism 21. One end of the discharge passage 26 (i.e., right end in the drawing) is communicated through an inner chamber 27 of the handpiece 10 and then a discharge hole defined in the handpiece 10 into the atmosphere. The other end of the discharge passage 26 (i.e., left end in the drawing) is an air outlet 28 which opposes the cutting tool rotating mechanism 21 below the air inlets 25.

[3] Internal Housing

Figure 7:
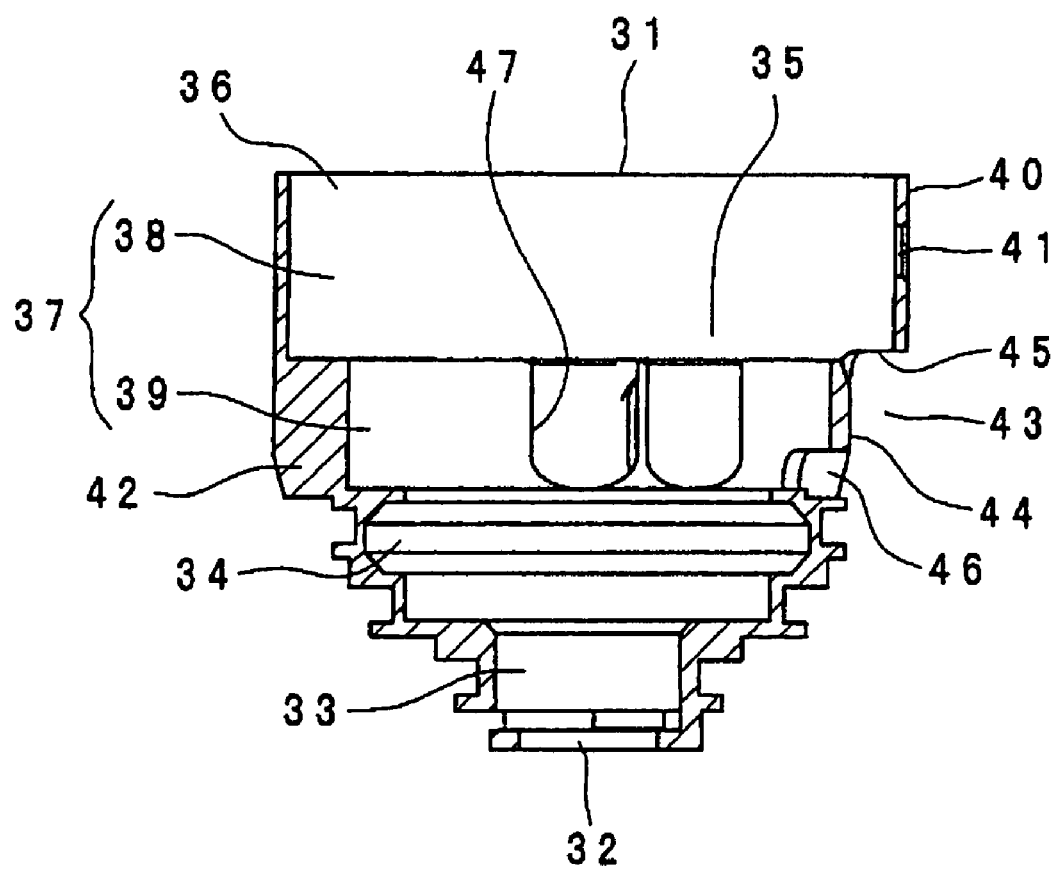
FIG. 7 is a vertical cross sectional view of the internal housing.
Figure 9:
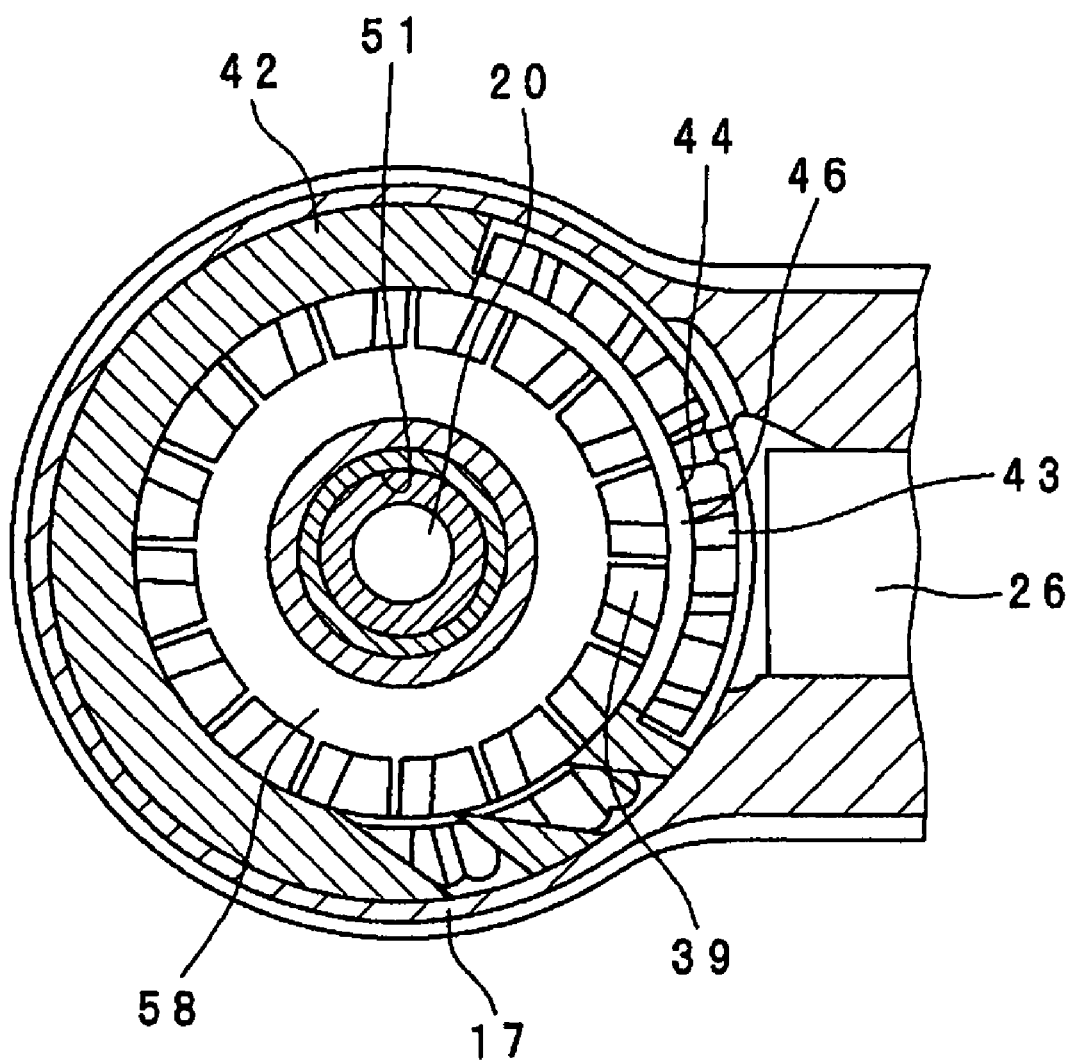
FIG. 9 is a cross sectional view taken along line A-A in FIG. 2.

An internal housing 30 is mounted within the external housing 17, for accommodating the cutting tool rotating mechanism 21. As shown in detail in FIGS. 4-7, the internal housing 30, which is a cylindrical member with top and bottom openings 31 and 32, has a plurality of cylindrical chambers including a tool-support receiving chamber 33, a lower-bearing receiving chamber 34, a wheel receiving chamber 35, and an upper-bearing receiving chamber 36 defined therein in this order from below and positioned coaxially with each other. As shown in FIG. 7, a portion 37 of the housing defining a lower part of the wheel receiving chamber 35 and another regions adjacent thereto has an upper larger diameter chamber 38 and a lower smaller diameter chamber 39 defined therein. A thin, annular portion 40 defining the upper larger diameter chamber 38 has an air-supply communication slot or opening 41 extending through internal and external circumferential surfaces thereof. Also, a thick annular portion 42 defining the lower smaller diameter chamber 39 is cut from outside to define a circumferential arcuate recess 43 extending radially inwardly and a circumferential arcuate wall 44 defining a there inside a part of the smaler diameter chamber 39. The arcuate recess 43 is communicated through an opening 45 defined thereabove to the larger diameter chamber 38 and the also communicated through an opening 46 provided below the arcuate wall 44 to the smaller diameter chamber 39. Referring to FIG. 9 showing a cross section taken along line A-A in FIG. 2, it can seen that the lower portion of the arcuate recess 43 is communicated through the opening 46 below the arcuate wall 44 to a space defined outside a lower turbine blade 58 accommodated within the smaller diameter chamber 39. This causes that, when the internal housing 30 is mounted within the external housing 17, the space outside the lower turbine blade 58 accommodated in the smaller diameter chamber 39 is communicated to the discharge passage 26.

Figure 4:
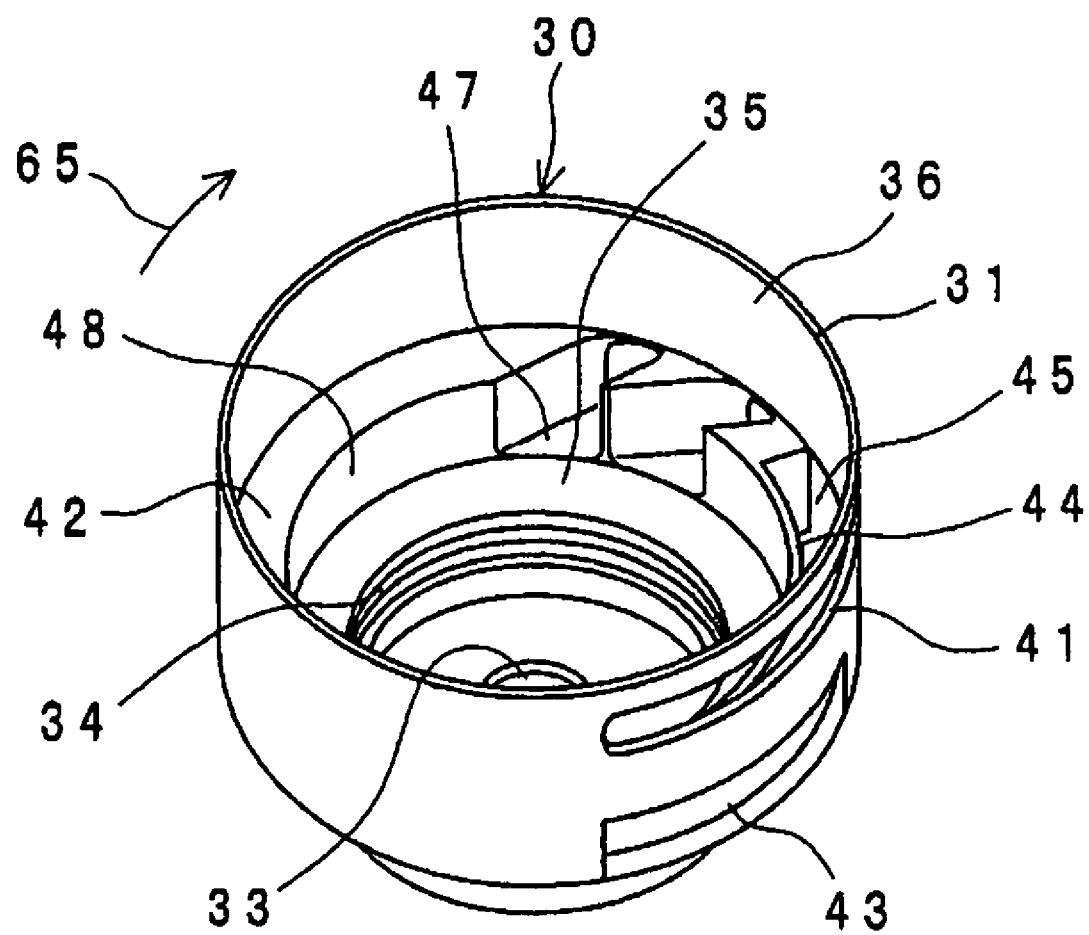
FIG. 4 is a perspective view of an internal housing.
Figure 5:
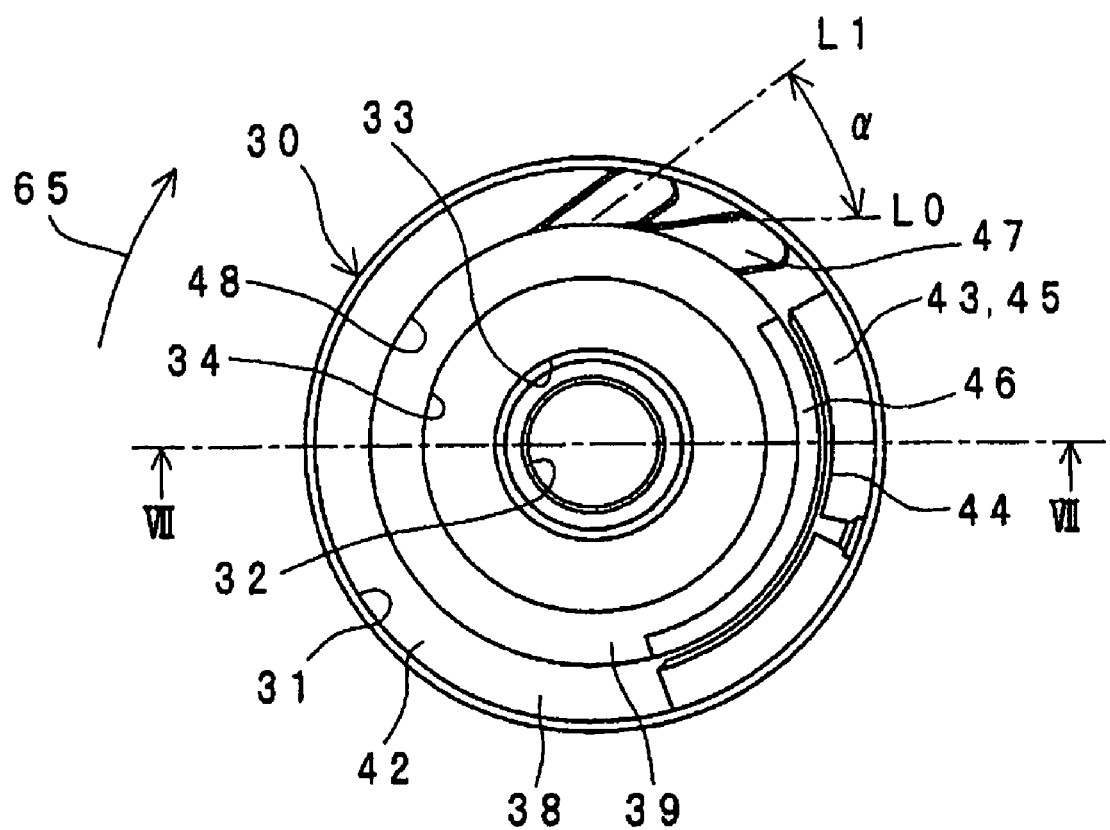
FIG. 5 is a plan view of the internal housing.
Figure 6:
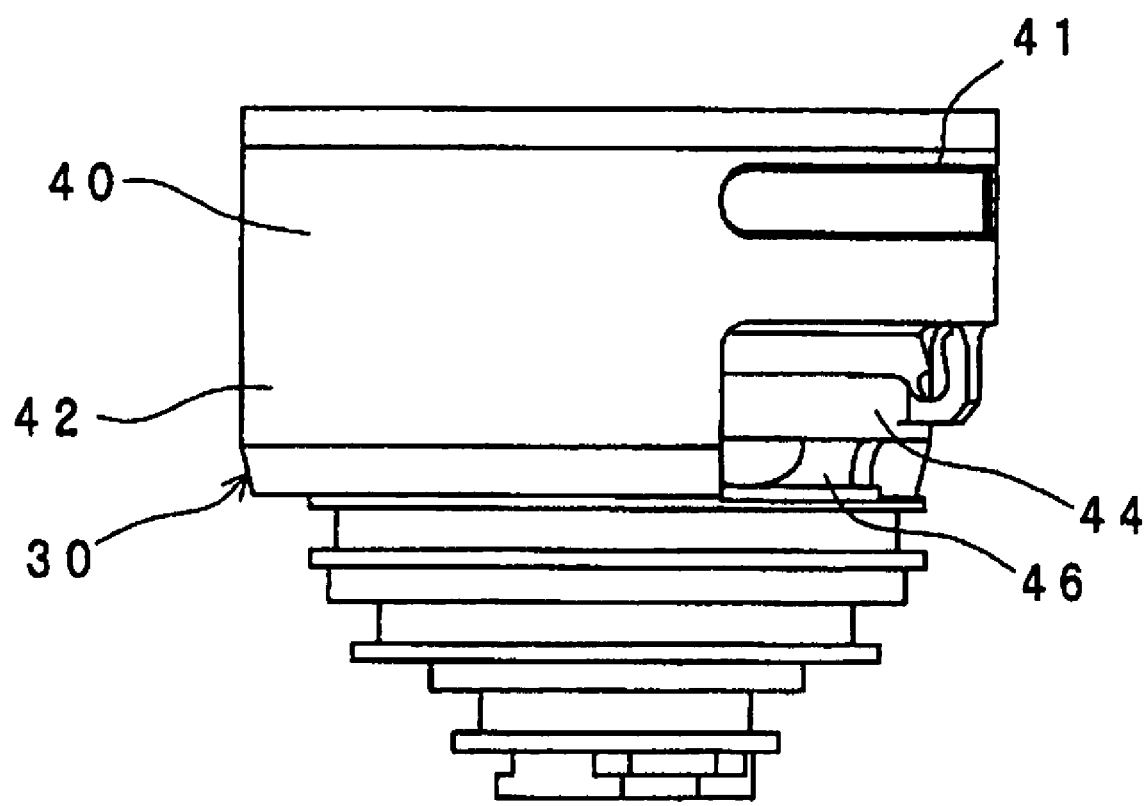
FIG. 6 is a side elevational view of the internal housing.

Referring to FIGS. 4 and 5, a plurality of buffer chambers 47 in the form of groves are defined in the portions of the thick annular portion 42 on the upstream side of the circumferential wall 44 with respect to the rotational direction of the cutting tool, extending from the inner circumferential surface to the outer circumferential surface of the thick annular portion 42 and opened to the bottom of the enlarged diameter portion 38. In the embodiment, two buffer chambers 47 are formed. Also, in the embodiment, each of the buffer chambers 47 is so oriented that a center line L1 of the buffer chamber 47 intersects with a corresponding tangential line LO of the inner peripheral surface 48 of the lower smaller diameter chamber 39 to define an acute angle α of 30-60 degrees outside the inner circumferential surface 48 and on the downstream side of the center line L1 with respect to the rotational direction of the cutting tool (i.e., clockwise direction). As shown in FIG. 2, the internal housing 30 so constructed is mounted within the interior of the external housing 17. In this position, the air-supply communication opening 41 opposes the air inlets 25 of the head 15. Also, the arcuate recess 43 and the circumferential wall 44 oppose the air outlet 28 of the head 15. A plurality of sealing rings or O-rings 47a are installed between the internal housing 30 and the external housing 17 to seal possible gaps defined therebetween. Different from the illustration shown in FIGS. 4 and 5, the buffer chambers 47 are illustrated in FIG. 2 as they are positioned to oppose the air-supply communication opening 41 within the internal housing 30, which simply aims to provide better understanding of the airflow in the buffer chambers 47 in light of FIG. 2. Of course, instead of arranging the buffer chambers 47 in such positions shown in FIGS. 4 and 5, they may be take positions shown in FIG. 2. Also, one or more additional buffer chambers may be provided in such positions shown in FIG. 2.

[4] Cutting Tool Rotating Mechanism

As shown in FIG. 2, the cutting tool rotating mechanism 21 accommodated within the internal housing 30 has a tool holder 50 for holding the cutting tool 20 along the rotational axis 19. The tool holder 50 has an elongated hole (tool holding hole) 51 defined therein and extending vertically from its bottom end and a chucking mechanism (not shown) for releasably chucking and holding the cutting tool 20 inserted in the hole 51, so that when tool holder 50 is placed in the cutting tool receiving chamber 33, it is supported by lower and upper bearings 52 and 53 placed within the lower and upper bearing receiving chambers 34 and 36, respectively, for rotation about the rotational axis 19. In the embodiment, the upper bearing 53 is mounted within an annular bearing housing 54 through which the it is secured to the internal housing 30. This arrangement allows that the cutting tool 20 is releasably inserted through the opening 32.

Figure 8:
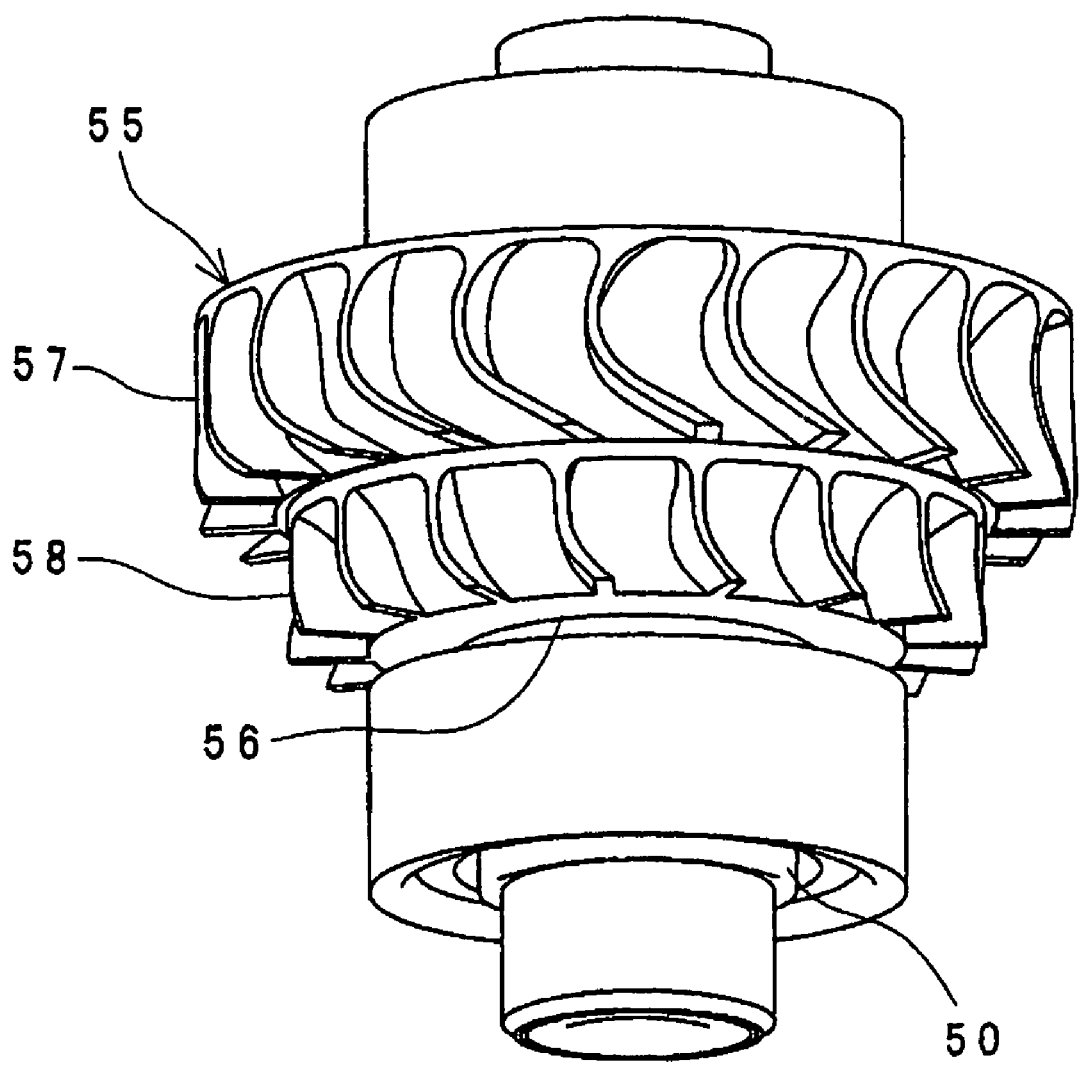
FIG. 8 is a perspective view of a rotor.

Positioned between the lower and upper bearings 52 and 53 is a rotor (wheel) 55 capable of using the pressurized air ejected from the inlets 25 to make rotations thereof to be transmitted through the holder 50 to the cutting tool 20. As shown in detail in FIG. 8, the rotor 55, which is substantially in the form of ring, has a central through-hole 56 into which the holder 50 is securely inserted. In the embodiment, the rotor 55, which is so-called a double-blade rotor, has larger diameter upper turbine blades 57 accommodated within the larger diameter chamber 38 (see FIG. 7) and smaller diameter lower turbine blades 58 accommodated within the smaller diameter chamber 39 (see FIG. 7). As shown in FIG. 2, when accommodated within the internal housing 30, the upper turbine blades 57 oppose the air-supply communication opening 41 and the air inlets 25 and the lower turbine blades 58 oppose the buffer chambers 47 and the circumferential wall 44 defined in the internal housing 30. In particular, regarding the lower turbine blades 58 and the circumferential wall 44, the circumferential wall 44 opposes an entire top-to-bottom length of the circumferential part of the lower turbine blades 58, so that an opposing region H of the lower turbine blades 58 and the air outlet 28 is in part or in whole occupied by the circumferential wall 44. This prevents the air rotating with the rotation of the lower turbine blades 58 from being forced directly into the air outlet 28 due to the centrifugal force applied thereto during the rotation.

Mounted on the internal housing 30 and within the interior of the external housing 17 are annular external and internal fixing rings 60 and 61 by which a cap 62 is retained to cover the tool rotating mechanism 21. The cap 62 is biased upward by a spring 63 mounted therebelow. This allows that the chucking mechanism is unlocked and locked for the exchange of the cutting tools 20 by pressing the cap 62 down against the biasing force from the spring 63 and releasing the pressed cap 62, respectively.

[5] Operation of Handpiece

In cutting operation of the teeth with the handpiece 10 so constructed, a cutting tool 20 suitable for the operation is selected and then mounted into the holder 50 from its bottom. Then, the pressurized air from the pressurized-air supply (not shown) is ejected through the air supply passages 23, the air inlets 25, and the air-supply communication opening, 41 onto the upper turbine blades 57, causing the rotor 55 to rotate in the direction indicated by the arrow 65 in FIGS. 3-5.

As shown in FIG. 2, the pressurized air impinged on the upper turbine blades 57 is then transported in the rotational direction with the rotation of the rotor 55 and then supplied to the lower turbine blades 58 where it impinges on the lower turbine blades 58 to provide further rotational force to the rotor 55. Subsequently, the pressurized air is transported into the arcuate recess 43 through the opening 46 underneath the circumferential wall 44 and then discharged through the air outlet 26 and the discharge passage 26 into the internal chamber 27 of the handpiece 10. The pressurized air in the internal chamber 27 is then discharged into the atmosphere through a discharge hole (not shown). A part of the pressurized air rotating with the lower turbine blades 58 is compressively forced into the buffer chambers 47 formed in the internal housing 30 due to the centrifugal force acting thereto. Since each butter chamber 47 is so oriented that the center line L1 of the buffer chamber 47 intersects with the tangential line L of the inner circumferential surface 48 of the lower smaller diameter chamber 39 with the angle α of 30-60 degrees, for example, the pressurized air rotating with the lower turbine blades 58 is effectively forced into and compressed in the buffer chamber 47. This results in that the interior of each buffer chamber 47 is pressurized. The pressurized air in the buffer chamber 47 flows under the lower turbine blades 58 and through the spaces in the lower bearing 52, the gaps between the internal housing 30 and the holder 50, and the lowermost end opening 68 of the external housing 17 and/or the holder receiving chamber 33 into the atmosphere.

[6] Sucking-Back Prevention

Halting the supply of the pressurized air means that no further fresh pressurized air is supplied from the inlets 25 to the rotor 55. However, the rotating rotor 55 maintains rotations thereof due to the inertial force. This cause the air rotating with the rotor 55 to be centrifugally forced into the buffer chambers 47 to increase the pressure of the interiors of the buffer chambers 47. The above discussed orientation of the buffer chambers 47 allows even the inertial rotations of the rotor 55 to effectively force the rotating air into the buffer chambers 47 and thereby to maintain the pressure in the buffer chambers 47. The pressurized air in the buffer chambers 47 flows back into the spaces below the rotor 55 and then through the gaps 66 and 67 and the lower opening 68 of the external housing 17 and/or the tool receiving chamber 33 into the atmosphere. This air flow effectively prevents any invasion of the contaminations such as saliva, blood, and cutting debris of the patient, through the lower opening 68 of the external housing 17 and/or the tool receiving chamber 33 into the interior of the housing 17.

Assuming that there were not the circumferential wall 44. In this instance, the rotating air with the rotation of the rotor 55 would be forced directly into the air outlet 26, causing the atmospheric air to be sucked through the lower opening 68 and/or the tool-support receiving chamber 33 and the gaps 66 and 67 into the outlet 26 and thereby drawing the contaminations such as saliva, blood, and cutting debris of the patient adhering on the cutting tool 20 and existing therearound into the interior of the housing 17. According to the handpiece 10 of the present invention, however, the circumferential wall 44 existing in the region H where the outlet 28 opposes the rotor 55 ensures the rotating air to be discharged to the atmosphere without being forced into the outlet 26. This ensures that that no negative pressure would cause in the interior of the head in part or in whole and the interior is maintained under no or positive pressure, during or after the inertial rotation of the rotor 55.

Accordingly, the handpiece 10 is always maintained clean by the typical sterilization even without disassembling thereof. Also, the interior of the supply tube where it is considerably difficult to be sterilized is always maintained clean and free from contaminations which would otherwise be drawn in due to the sucking back. Further, no contamination such as cutting debris would be drawn into the interior of the housing 17 and accumulated in the chucking mechanism or bearings 52 and 53 of the tool support 50, which ensures the chucking and bearing mechanisms to be used in a stable manner for a long period of time. No invasion of the contaminations into the bearing ensures to maintain the precision of the bearing surfaces which would otherwise cause the generation of noises. Furthermore, according to the invention the sucking back is prevented by the fixed elements such as the circumferential wall 44, the buffer chambers 47, and passages 66, 67, 68 and 34, rather than employing movable elements, which ensures a reliable sucking-back prevention for a long time.

For the handpiece 10 of the present invention with the circumferential wall and the buffer chambers and the conventional handpieces without the circumferential wall or buffer chambers, the pressure in the outlet was measured immediately after the halt of the supply of pressurized air, i.e., during the inertial rotations of the rotor. As a result, no negative pressure was detected in the handpiece according to the present invention, but the negative pressure at about 10-400 mmAq was detected in the outlets in the conventional handpieces. This test shows that the sucking-back is effectively prevented in the handpiece of the present invention.

[7] Modifications

Although the circumferential wall 44 covers the entire opposing region H of the rotor 55 and the outlet 28 in the previous embodiment, it is not necessary to do so and the rotor 55 and the outlet 28 may oppose in part directly provided that the sucking-back can be effectively prevented during the inertial rotations of the rotor 55.

Also, although the double-blade rotor 55 is used in the previous embodiment, a sigle-blade rotor may be used instead.

Further, a single housing head in which the internal and external housings 30 and 17 are integrated as a single unit may be used instead.

What is claimed is:

1. A handpiece, comprising:
    a gripping portion to be gripped by an operator;
    a head mounted at a distal end of the gripping portion; and
    a wheel rotatably mounted in an interior of the head, said wheel comprising upper and lower turbine blades;
    wherein the head having
        an inlet from which pressurized air is supplied to the wheel and an outlet from which the pressurized air is discharged, the inlet and outlet being defined in the head;
        at least one buffer chamber defined in the head, where the pressurized air is forced in due to a centrifugal force applied thereto by rotations thereof with the wheel and then accumulated under positive pressure;
        a passage for guiding the accumulated air from a neighborhood of the rotating wheel to an atmosphere; and
        a circumferential wall extending circumferentially between the outlet and the wheel for providing a resistance to the air moving from the wheel toward the outlet, the circumferential wall substantially occupying a region where the outlet opposes the wheel, opposing an entire top to bottom part of a circumferential part of said lower turbine blades and defining an arcuate cavity between the circumferential wall and the outlet so that, during an operation in which the pressurized air is supplied from the inlet, the pressurized air from the wheel travels beyond the circumferential wall into the arcuate cavity and then into the outlet and, after halting a supply of the pressurized air from the inlet, the circumferential wall resists the pressurized air from the wheel from being directly forced into the outlet.

2. The handpiece of claim 1, wherein the at least one buffer chamber is opened to oppose a rational direction of the wheel.

3. The handpiece of claim 2, wherein the head has an external housing and an internal housing, the external housing having an interior within which the internal housing is releasably mounted, the internal housing having an interior within which the wheel is accommodated, the at least one buffer chamber and the circumferential wall being formed on the internal housing.

4. The handpiece of claim 1, wherein the at least one buffer chamber is oriented to a direction defining an angle of about 30-60 degrees with a tangential line defined on a circle drawn by a rotating outermost edge of the wheel.

5. The handpiece of claim 4, wherein the at least one buffer chamber is formed adjacent to and on an upstream side of the outlet with respect to the rotation of the wheel.

6. A method for preventing sucking-back, comprising:
    rotatably mounting a wheel in a head mounted at a distal end of a gripping portion to be gripped by an operator;
    rotating the wheel comprising upper and lower turbine blades and a tool held by the wheel using an air ejected from an inlet; and
    discharging the air rotating with the wheel through an outlet;

wherein, during an inertial rotation of the wheel after a halt of an air ejection from the inlet to the wheel,
causing the air rotating with the wheel to be compressively forced into a buffer chamber formed outside the wheel due to a centrifugal force applied thereto;
discharging the compressed air radially outwardly from the tool through a passage formed in the head to an atmosphere; and
restricting a flow of the air moving from the wheel to the outlet by a circumferential wall opposed to an entire top to bottom part of a circumferential part of said lower turbine blades and provided between the wheel and the outlet to define an arcuate cavity between the circumferential wall and the outlet so that, during a normal operation, the air is moved from the wheel beyond the circumferential wall into the arcuate cavity and then into the outlet.

* * * * *